US009227937B2

(12) United States Patent
Chambers et al.

(10) Patent No.: US 9,227,937 B2
(45) Date of Patent: Jan. 5, 2016

(54) PHENOXYALKYL PYRIDINIUM OXIME THERAPEUTICS FOR TREATMENT OF ORGANOPHOSPHATE POISONING

(75) Inventors: Janice E. Chambers, Starkville, MS (US); Howard W. Chambers, Starkville, MS (US); Edward C. Meek, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 444 days.

(21) Appl. No.: 13/261,513

(22) PCT Filed: May 12, 2011

(86) PCT No.: PCT/US2011/000842
§ 371 (c)(1),
(2), (4) Date: Mar. 1, 2013

(87) PCT Pub. No.: WO2011/142826
PCT Pub. Date: Nov. 17, 2011

(65) Prior Publication Data
US 2013/0172393 A1      Jul. 4, 2013

Related U.S. Application Data

(60) Provisional application No. 61/395,343, filed on May 12, 2010.

(51) Int. Cl.
*C07D 213/53*   (2006.01)
*A61K 31/4425*  (2006.01)

(52) U.S. Cl.
CPC .......... *C07D 213/53* (2013.01); *A61K 31/4425* (2013.01)

(58) Field of Classification Search
CPC .................. C07D 213/53; A61K 31/4425
USPC .................... 514/640, 357; 546/338
See application file for complete search history.

(56) References Cited

U.S. PATENT DOCUMENTS 4,352,810 A    10/1982   Benschop et al.

FOREIGN PATENT DOCUMENTS

WO    WO2005027905 A1    3/2005

OTHER PUBLICATIONS

Jokanovic, et al: "Current Underst. . . . Organ. Poisoning"; European Journal of Pharmacology, Elsevier Science, NL, vol. 553, No. 1-3, Dec. 28, 2006, pp. 10-17.
Chambers, et al: "Testing of Novel . . . Nerve Agent Surrogates"; Chemico-Biological Interactions, vol. 203, 2013, pp. 135-138.

*Primary Examiner* — Barbara P Badio
*Assistant Examiner* — Sara E Townsley
(74) *Attorney, Agent, or Firm* — Butler Snow LLP (57) ABSTRACT

Phenoxyalkyl pyridinium oxime compounds for use in treating organophosphate poisoning.

20 Claims, 3 Drawing Sheets

PHENOXYALKYL PYRIDINIUM OXIME THERAPEUTICS FOR TREATMENT OF ORGANOPHOSPHATE POISONING

CROSS-REFERENCE TO RELATED APPLICATIONS

The present application claims the benefit of priority from U.S. Patent Application No. 61/395,343, titled "Novel Oxime Therapeutics for Organophosphate Anticholinesterase Poisoning" and filed on May 12, 2010, the entire contents of which are hereby incorporated by reference in their entirety.

STATEMENT OF GOVERNMENT SUPPORT

This invention was made with government support under FA850-05-2-6518 awarded by the United States Air Force/AFMC. The U.S. government may have certain rights in the invention.

BACKGROUND OF THE INVENTION

Organophosphorus (OP) compounds, which have been used as chemical warfare agents (CWAs), inhibit acetylcholinesterase (AChE) in neural synapses, glands, and neuromuscular junctions. This action results in an accumulation of excess acetylcholine which, at lethal levels, will lead to death from respiratory failure (Sidell, 1997). High level OP poisoning with CWAs can result in seizures from the excessive central hyperexcitability, leading to short-term incapacitation and long-term brain damage. CWA exposure has resulted in deficits in psychomotor function and memory, as evidenced in humans exposed to sarin in the Japanese terrorist attacks (Nishiwaki et al., 2001; Miyaki et al, 2005).

Chemotherapy for OP poisoning typically involves the administration of atropine, a muscarinic receptor antagonist, and an oxime (e.g., 2-PAM), an AChE reactivator (Dunn et al., 1997). While other approaches have been investigated for the treatment of OP poisoning, oxime therapy to rescue inhibited AChE still appears to be an essential therapeutic.

AChE reactivation by oximes occurs through nucleophilic attack on the OP moiety bound to the enzyme. The administration of an oxime must occur before the inhibited AChE has "aged", a non-enzymatically mediated dealkylation reaction that renders the inhibited enzyme refractory to either spontaneous or oxime-mediated reactivation. The time course of this AChE aging is compound dependent, with a compound such as soman displaying very rapid aging. Therefore, for oxime therapy to be effective, it generally needs to be administered and delivered to the inhibited AChE quickly after CWA exposure, before appreciable proportions of the inhibited AChE ages.

A number of oximes have been synthesized and tested as AChE reactivators since the initial discovery of 2-PAM (Wilson and Ginsberg, 1955), including bis-pyridinium oximes containing at least one pyridine-2- or -4-aldoxime moiety (Worek et al., 1996; Kassa and Cabal, 1999; Chen et al., 2001; Kuca and Kassa, 2004; Kim et al., 2005; Kuca et al., 2005; Petroianu et al., 2006). Despite years of research, however, 2-PAM and obidoxime remain the most widely-used AChE reactivators (Sidell, 1997).

A significant limitation to the value of existing oximes is their lack of effectiveness in the brain. This limitation is due to the inability of large highly polar molecules to cross the blood-brain barrier. The existing oximes can allow OP poisoning victims to survive, by reactivating the phosphorylated AChE in the peripheral nervous system (e.g., in the diaphragm and lungs), while the brain AChE remains substantially inhibited for an extended period of time. A recent study used microdialysis and HPLC to detect 2-PAM in the brain of rats following intravenous administration of the oxime. However, the level found in the brain was only about 10% of that in the blood (Sakurada et al., 2003).

Due to the limited ability of 2-PAM to cross the blood brain barrier and reactivate brain AChE, a pro-drug form of 2-PAM, pro-PAM, was synthesized. Initial studies with pro-PAM suggested increased brain AChE activity (Clement, 1979); however, subsequent studies demonstrated that pro-PAM was more toxic than 2-PAM. Additionally, pro-PAM's ability to reactivate brain AChE was dependent on the rate at which the drug was transported to the CNS, with intravenous administration producing the only significant brain AChE reactivation (Kenley et al, 1982). Therefore, pro-PAM, requiring intravenous administration, is not practical for poisonings occurring on the field of battle. Additionally, a drug requiring metabolic activation in a tissue (i.e., brain) known for its low levels of drug metabolizing enzymes, is not ideal for rapid therapy against agents, such as soman, which result in rapid aging of phosphorylated AChE.

Reactivating OP-inhibited AChE in the brain is important, as OP compounds can have adverse effects on memory for years after a poisoning incident. Studies in laboratory animals have indicated that neurochemical aberrations persist well after the initial exposure to insecticidal OP's and well after the AChE activity has recovered to normal levels (Richardson and Chambers, 2003, 2004, 2005; Tang et al., 1999, 2003). Long-term memory deficits have likewise been reported in the victims of terrorist attacks with sarin in Japan (Nishiwaki et al., 2001; Miyaki et al., 2005). Such long-term effects on brain chemistry and on behavior, undoubtedly resulting from impacts of poisoning on the brain, would be expected to be exacerbated if the AChE inhibition were prolonged. Returning AChE activity to normal levels quickly, in order to rapidly return a subject's neurochemistry to normal, would be expected to reduce both short-term and long-term physiological and behavioral effects. Therefore, an antidote effective in the brain should be extremely valuable in not only survival of lethal dose exposures, but also returning a subject to normalcy as quickly as possible.

SUMMARY OF THE INVENTION

The present compounds, useful in preparing pharmaceutical compositions for treating exposure to organophosphate compounds, have the following formula:

and include derivatives thereof. In these compounds, R is hydrogen, alkyl, alkenyl, aryl, acyl, nitro, or halo; n is 3, 4, or 5; and X is a pharmaceutically acceptable anion. R can be, for example, a hydrogen, methyl, ethyl, phenyl, methoxy, ethoxy, trimethyl, methylchloro, diethyl, diethylchloro, ethylchloro, phenoxy, acetyl, benzoyl, bromo, chloro, iodo, dichloro, or trichloro substituent, or a combination of any of the foregoing. X is preferably a halo moiety, such as a bromine ion. Particular compounds within the scope of the present invention are listed in Table 1 below.

The present compounds are preferably formulated as pharmaceutical compositions, and can be used to reactivate phosphorylated brain acetylcholinesterase that has been inhibited by at least one organophosphorous compound. In this way, the effects of exposure to an organophosphate compound can be treated, i.e. by administering a therapeutically effective amount of such pharmaceutical compositions to a subject in need thereof. The compositions can be administered via a variety of administrative routes, such as intravenously, and can be administered to a subject prior to or following exposure of the subject to an organophosphate compound. The organophosphate compound can be, for example, an organophosphate insecticide or a nerve agent such as sarin, soman, tabun, or VX.

DETAILED DESCRIPTION OF THE INVENTION

Definitions

As used herein, the following terms and variations thereof have the meanings given below, unless a different meaning is clearly intended by the context in which such term is used.

"Acyl" refers to a group of the form RCO—, where R is an organic group. The term "aroyl" refers to the group —C(O)R, where R is aryl. Similar compound radicals involving a carbonyl group and other groups are defined by analogy. The term "aminocarbonyl" refers to the group —NHC(O)—. The term "oxycarbonyl" refers to the group —OC(O)—.

"Alkyl" refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "heteroalkyl" refers to carbon-containing straight-chained, branch-chained and cyclic groups, all of which can be optionally substituted, containing at least one O, N or S heteroatom. The term "alkoxy" refers to the ether —O-alkyl, where alkyl is defined as above.

"Alkenyl" refers to unsaturated groups which contain at least one carbon-carbon double bond and includes straight-chain, branched-chain, and cyclic groups, all of which can be optionally substituted. Preferable alkenyl groups have 1 to 10 carbon atoms. The term "heteroalkenyl" refers to unsaturated groups which contain at least one carbon-carbon double bond and includes straight-chained, branch-chained and cyclic groups, all of which can be optionally substituted, containing at least one O, N or S heteroatom.

"Anion" refers to an atom, molecule, or group of molecules having a net negative electrical charge.

"Aryl" refers to aromatic groups that have at least one ring having a conjugated, pi-electron system and includes carbocyclic aryl and biaryl, both of which can be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5-14 membered cyclic unsaturated radicals containing one, two, three, or four O, N, or S heteroatoms and having 6, 10, or 14 π-electrons delocalized in one or more rings, e.g., pyridine, oxazole, indole, thiazole, isoxazole, pyrazole, pyrrole, each of which can be optionally substituted as discussed above.

"Central nervous system" refers to the part of the nervous system that includes the brain and spinal cord. The central nervous system does not include the peripheral nerves which carry signals between the central nervous system and the muscles and organs of the body.

"Derivative" refers to a compound that is modified or partially substituted with another component.

"Halo" refers to fluoro-, chloro-, bromo-, or iodo-substitutions. The term "alkanoyl" refers to the group. —C(O)R, where R is alkyl.

"Hydrocarbyl" refers to a hydrocarbon chain, which can be optionally substituted or provided with other substitutions known to the art.

"Organophosphate compounds" refer to esters of phosphoric acid which act on the enzyme acetylcholinesterase and have neurotoxicity. Such compounds include nerve agents such as tabun (Ethyl N,N-dimethylphosphoramidocyanidate, also referred to as GA), sarin (O-Isopropyl methylphosphonofluoridate, also referred to as GB), soman (O-Pinacolyl methylphosphonofluoridate, also referred to as GD), and VX (O-ethyl-S-[2(diisopropylamino)ethyl]methylphosphonothiolate), as well as some compounds used as insecticides, such as phosphoric acid diethyl 4-nitrophenyl ester (paraoxon), diethyl-p-nitrophenyl monothiophosphate (parathion) and phosphorothioic acid O-(3-chloro-4-methyl-2-oxo-2H-1-benzopyran-7-yl) O,O-diethyl ester (coumaphos).

"Pharmaceutically acceptable" refers to any element, compound, or other molecule which does not interfere with the effectiveness of the biological activity of the present compounds and that is not toxic to the subject to which it is administered.

A "subject" refers a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treat" and "treatment," with respect to the exposure of a subject to an organophosphate compound, refer to a medical intervention which attenuates, prevents, and/or counteracts the effects of such exposure. The foregoing terms can refer to the prophylactic administration of the present compounds and compositions to subjects at risk of exposure to an organophosphate compound prior to an anticipated exposure, and/or can refer to the administration of the present compounds and compositions following such exposure.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Compounds

The present compounds comprise a series of novel phenoxyalkyl pyridinium oximes that are capable of crossing the blood-brain barrier and therefore are capable of reactivating acetylcholinesterase (AChE) in the brain that has been inhibited by organophosphate anticholinesterases. The oxime therapeutics that currently exist, such as 2-PAM (pralidoxime), are incapable of reactivating brain acetylcholinesterase because they cannot penetrate the blood-brain barrier appreciably and, therefore, result in seizures and brain damage in subjects exposed to organophosphate compounds. The ability of the present compounds to cross the blood-brain barrier allows them to prevent or attenuate brain damage induced by organophosphates such as nerve agents by entering the brain and reactivating the inhibited acetylcholinesterase, thereby hastening recovery from the poisoning and preventing or attenuating the seizures so that brain damage will be less likely.

Even when delivered to the brain, some drugs, such as pro-PAM, must be metabolically activated in order to produce active compounds such as 2-PAM in situ in the brain, but since the brain typically has only low activities of drug metabolizing enzymes, the activation of such pro-drugs will be slow, limiting their ultimate effectiveness. By contrast, the present oximes are sufficiently able to penetrate the blood-brain barrier and are therefore effective as soon as they enter the brain, thereby producing a more effective antidote to organophosphorous compound poisoning.

One challenge in producing an oxime capable of crossing the blood-brain barrier is that the pyridinium moiety of the oxime, which is believed to be important in effecting AChE reactivation, is charged, and charged molecules generally have difficulty crossing the blood brain barrier. The present oximes therefore have increased lipophilicity, in order to enhance the ability of such molecules to pass into the brain. Lipophilicity can be determined experimentally by several methods, one of which is the octanol-water/buffer partition coefficient (Gulyaeva et al., 2003), a well-accepted, relatively easy method suitable for rapid screening of compounds.

The present invention has both military and civilian applicability. Presently, if fighters are attacked with nerve agents in battle or civilians are under terrorist attack by nerve agents, the acetylcholinesterase in the brain will be inhibited by the nerve agent and the resultant seizures may cause permanent brain damage, with subsequent long term and cognitive deficits. The present oximes, by penetrating into the brain and reactivating the inhibited brain acetylcholinesterase, should prevent or attenuate the seizures, thereby preventing or attenuating any brain damage. This beneficial result will provide both battlefield advantages to the military and long-term health benefits to both military personnel and civilians. Additionally, these novel therapeutics also have efficacy for organophosphate insecticide poisoning and have applications in the therapy of industrial and/or agricultural insecticide poisonings.

The present phenoxyalkyl oxime therapeutics have the following structure:

R can be any of a number of moieties, in particular hydrogen or an alkyl, alkenyl, aryl, acyl, nitro, or halo moiety. R can, for example, be methyl, ethyl, phenyl methoxy, ethoxy, trimethyl, methylchloro, diethyl, diethylchloro, ethylchloro, phenoxy, acetyl, benzoyl, bromo, chloro, iodo, dichloro, or trichloro. The alkyl chain linking the aryl and pyridinium moieties can be three, four, or five carbons long, such that n is 3, 4, or 5. The X moiety is a pharmaceutically acceptable anion, and is preferably a halo atom such as bromine. In preferred embodiments, R is 4-Ph-$CH_2$—O— and n is 4 (oxime 59 in table 1 below) or 4-Cl— (oxime 14).

Representative phenoxyalkyl pyridinium oxime compounds of the present invention are described in Table 1, with reference to the foregoing formula.

TABLE 1

Phenoxyalkyl Pyridinium Oximes

| Oxime No. | R | n |
|---|---|---|
| 1, 2, 3 | H— | 3, 4, 5 |
| 4, 5, 6 | 4-$CH_3$— | 3, 4, 5 |
| 7, 8, 9 | 2,6-($[CH_3]_2CH)_2$— | 3, 4, 5 |
| 10, 11, 12 | 4-$CH_3$—O | 3, 4, 5 |
| 13, 14, 15 | 4-Cl— | 3, 4, 5 |
| 16, 17, 18 | 4-Br— | 3, 4, 5 |
| 19, 20, 21 | 4-$O_2$N— | 3, 4, 5 |
| 22, 23, 24 | 3-$O_2$N— | 3, 4, 5 |
| 25, 26, 27 | 4-$CH_3$C(:O)— | 3, 4, 5 |
| 28, 29, 30 | 4-$CH_3CH_2$C(:O)— | 3, 4, 5 |
| 31, 32, 33 | 3-CH=CHCH=CHCH-4 | 3, 4, 5 |
| 34, 35, 36 | 4-Ph | 3, 4, 5 |
| 37, 38, 39 | 2,3,5-($CH_3)_3$— | 3, 4, 5 |
| 40, 41, 42 | 2,4,6-($CH_3)_3$— | 3, 4, 5 |
| 43, 44, 45 | 3-$CH_3$-4-Cl— | 3, 4, 5 |
| 46, 47, 48 | 4-Ph—C(:O)— | 3, 4, 5 |
| 49, 50, 51 | 2,5-$Cl_2$— | 3, 4, 5 |
| 52, 53, 54 | 4-Ph—O— | 3, 4, 5 |
| 55, 56, 57 | 4-Ph—$CH_2$— | 3, 4, 5 |
| 58, 59, 60 | 4-Ph—$CH_2$—O— | 3, 4, 5 |
| 61, 62, 63 | 2,4,5-$Cl_3$— | 3, 4, 5 |
| 64, 65, 66 | 4-Ph—$CH_2$C(:O)— | 3, 4, 5 |
| 67, 68, 69 | 2,4,6-$Cl_3$— | 3, 4, 5 |
| 70, 71, 72 | 3,4-$Cl_2$— | 3, 4, 5 |
| 73, 74, 75 | 2,6-$Cl_2$-4-$O_2$N— | 3, 4, 5 |
| 76, 77, 78 | 4-Cl-3,5-($CH_3)_2$— | 3, 4, 5 |
| 79, 80, 81 | 3-Ph— | 3, 4, 5 |
| 82, 83, 84 | 3-$CH_3CH_2$-4-Cl— | 3, 4, 5 |
| 85, 86, 87 | 3-O—C(:O)—CH=C($CH_3$)-4 | 3, 4, 5 |
| 88, 89, 90 | 2-$CH_3$-4-($CH_3)_3$C— | 3, 4, 5 |
| 91, 92, 93 | 2,4-[($CH_3)_3$C—]$_2$— | 3, 4, 5 |
| 94, 95, 96 | 4-$CH_3CH_2$C($CH_3)_2$— | 3, 4, 5 |
| 97, 98, 99 | 4-($CH_3)_3$CC$H_2$C($CH_2)_2$— | 3, 4, 5 |
| 100, 101, 102 | 2-Br-4-Cl— | 3, 4, 5 |
| 103, 104, 105 | 2-Cl-4-Br— | 3, 4, 5 |
| 106, 107, 108 | 2-Br-4-$CH_3$— | 3, 4, 5 |
| 109, 110, 111 | 4-Br-3,5-($CH_3)_2$— | 3, 4, 5 |
| 112, 113, 114 | 4-$CH_3(CH_2)_6$—O— | 3, 4, 5 |
| 115, 116, 117 | 4-Ph—C($CH_3)_2$— | 3, 4, 5 |
| 118, 119, 120 | 4-$CH_3$—O—$CH_2CH_2$— | 3, 4, 5 |
| 121, 122, 123 | 2,4-$Cl_2$— | 3, 4, 5 |

The present compounds preferably have a lipophilicity substantially greater than that of 2-PAM, which as noted above does not significantly cross the blood-brain barrier. Lipophilicity can be determined by measuring octanol:water partition coefficients.

Organophosphate Surrogates

The present oximes can preferably be tested using surrogates for nerve agents, which are highly dangerous for a researcher to handle. One such surrogate is phthalimidyl isopropyl methylphosphonate (PIMP), an analogue of the nerve agent sarin, which inhibits acetylcholinesterase and phosphorylates AChE with the same chemical moiety as does sarin. PIMP is very unstable in aqueous solution, degrading within about 15 minutes. This provides PIMP with the advantage in in vitro experiments of inhibiting acetylcholinesterase effectively but, because of its transience, being unable to re-inhibit any acetylcholinesterase that is reactivated by the subsequently-introduced oxime.

Another sarin surrogate that can be used is nitrophenyl isopropyl methylphosphonate (NIMP). This surrogate also leaves the AChE phosphorylated with the same moiety as sarin does, and is stable in aqueous solution and therefore is sufficiently stable to use in in vivo experiments, whereas PIMP is generally insufficiently stable to be used in vivo. Both of these surrogates are non-volatile and safer to personnel than the live agents.

Other compounds useful in testing the present phenoxyalkyl oximes include an analog of the nerve agent VX, nitrophenyl ethyl methylphosphonate (NEMP), useful as a surrogate for VX, which phosphorylates AChE with the same chemical moiety as does VX. The active metabolite of the insecticide parathion, paraoxon (PXN), phosphorylates AChE with the same chemical moiety as occurs after exposure to parathion and a variety of other OP insecticides, and thus can be used as a surrogate for such insecticides.

The structural similarities between sarin and the sarin surrogates PIMP and NIMP, between VX and the VX surrogate NEMP, and between parathion and its metabolite paraoxon (PXN) can be seen when these structures are compared. The chemical structures of the foregoing molecules are shown below.

sarin

NIMP

PIMP

VX

NEMP parathion paraoxon

Compound Properties

In general, the present compounds include salts and prodrug esters of the compounds described herein. It is well known that organic compounds have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound in the present application includes such salt forms as occur at physiological pH or at the pH of a pharmaceutical composition unless specifically excluded.

Similarly, prodrug esters can be formed by reaction of either a carboxyl or a hydroxyl group on the compound with either an acid or an alcohol to form an ester. Typically, the acid or alcohol includes an alkyl group such as methyl, ethyl, propyl, isopropyl, butyl, isobutyl, and tertiary butyl. These groups can be substituted with substituents such as hydroxy, halo, or other substituents. Such prodrugs are well known in the art. The prodrug is converted into the active compound by hydrolysis of the ester linkage, typically by intracellular enzymes. Other suitable groups that can be used to form prodrug esters are well known in the art.

A number of the present compounds are optically active, owing to the presence of chiral carbons or other centers of asymmetry. All of the possible enantiomers or diastereoisomers of such compounds are included herein unless otherwise indicated despite possible differences in activity. In addition, preferred compounds have a log P of from about 1 to about 4 to enhance bioavailability and, when desired, central nervous system (CNS) penetration.

Pharmaceutical Compositions

A pharmaceutical composition can comprise one or more of the present compounds. Such a composition preferably comprises: (1) a therapeutically effective amount of one or more of the present compounds (and/or salts and esters thereof); and (2) a pharmaceutically acceptable excipient.

A pharmaceutically acceptable excipient, including carriers, can be chosen from those generally known in the art including, but not limited to, inert solid diluents, aqueous solutions, or non-toxic organic solvents, depending on the route of administration. If desired, these pharmaceutical formulations can also contain preservatives and stabilizing agents and the like, for example substances such as, but not limited to, pharmaceutically acceptable excipients selected from the group consisting of wetting or emulsifying agents, pH buffering agents, human serum albumin, antioxidants, preservatives, bacteriostatic agents, dextrose, sucrose, trehalose, maltose, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other carriers also can be used.

Liquid compositions can also contain liquid phase excipients either in addition to or to the exclusion of water. Examples of such additional liquid phases are glycerin, vegetable oils such as cottonseed oil, organic esters such as ethyl oleate, and water-oil emulsions.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. The pharmaceutical compositions of the present invention can be formulated for administration by intravenous infusion, oral, topical, intraperitoneal, intravesical, transdermal, intranasal, rectal, vaginal, intramuscular, intradermal, subcutaneous and intrathecal routes.

Formulations of compound suitable for use in methods according to the present invention can be presented in unit-dose or multi-dose sealed containers, in physical forms such as ampules or vials. The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Preclinical Models and Clinical Evaluation

In order to screen for the most effective of the present compounds and pharmaceutical compositions and determine appropriate candidates for further development, as well as to determine appropriate dosages of such compounds and compositions for a human subject, preclinical animal models can be used. Exemplary animal models are set forth below. Preferably, a series of tests is performed in animal models to screen for activity in treating and/or preventing the effects of exposure to nerve agents.

Compounds and compositions are preferably selected using a panel of pre-clinical tests. Preliminary screening tests can be used to determine appropriate dosages to test in follow-on models. Appropriately selected doses of compounds and compositions tested in this way can then be subjected to testing for efficacy against nerve agent exposure.

Treatments

The effects of nerve agent exposure can be prevented or ameliorated by administering therapeutically effective amounts of one or more of the present compounds and/or pharmaceutical compositions to a patient in need thereof. The present compounds and/or compositions are administered to a patient in a quantity sufficient to treat or prevent the symptoms and/or the underlying etiology associated with nerve agent exposure in the patient. The present compounds can also be administered in combination with other agents known to be useful in the treatment of nerve agent exposure, such as atropine sulfate, diazepam, and pralidoxime (2-PAM), either in physical combination or in combined therapy through the administration of the present compounds and agents in succession (in any order).

Administration of the present compounds and compositions can begin immediately following exposure to an organophosphate nerve agent, preferably within the first hour following exposure, and more preferably within one to five minutes. Administration of the compositions and compounds can alternatively begin prior to an anticipated exposure (such as impending combat), in order to prevent or reduce the impact of subsequent exposure. The present invention thus includes the use of the present compounds and/or a pharmaceutical composition comprising such compounds to prevent and/or treat exposure to a nerve agent.

Depending upon the particular needs of the individual subject involved, the present compounds can be administered in various doses to provide effective treatments for nerve agent exposure. Factors such as the activity of the selected compound, half life of the compound, the physiological characteristics of the subject, the extent or nature of the subject's exposure or condition, and the method of administration will determine what constitutes an effective amount of the selected compounds. Generally, initial doses will be modified to determine the optimum dosage for treatment of the particular subject. The compounds can be administered using a number of different routes including oral administration, topical administration, transdermal administration, intraperitoneal injection, or intravenous injection directly into the bloodstream. Effective amounts of the compounds can also be administered through injection into the cerebrospinal fluid or infusion directly into the brain, if desired. In view of the long-term effects of low-dose exposure to nerve agents, it is contemplated that repeated doses of the present compounds administered over an extended period of time may be required.

An effective amount of any embodiment of the present invention is determined using methods known to pharmacologists and clinicians having ordinary skill in the art. For example, the animal models described herein can be used to determine applicable dosages for a patient. As known to those of skill in the art, a very low dose of a compound, i.e. one found to be minimally toxic in animals (e.g., 1/10×LD10 in mice), can first be administered to a patient, and if that dose is found to be safe, the patient can be treated at a higher dose. A therapeutically effective amount of one of the present compounds for treating nerve agent exposure can then be determined by administering increasing amounts of such compound to a patient suffering from such exposure until such time as the patient's symptoms are observed or are reported by the patient to be diminished or eliminated.

In a preferred embodiment, the present compounds and compositions selected for use in treating or preventing nerve agent exposure have a therapeutic index of approximately 2 or greater. The therapeutic index is determined by dividing the dose at which adverse side effects occur by the dose at which efficacy for the condition is determined. A therapeutic index is preferably determined through the testing of a number of subjects. Another measure of therapeutic index is the lethal dose of a drug for 50% of a population ($LD_{50}$, in a pre-clinical model) divided by the minimum effective dose for 50% of the population ($ED_{50}$).

Blood levels of the present compounds can be determined using routine biological and chemical assays and these blood levels can be matched to the route of administration and half life of a selected compound. The blood level and route of administration can then be used to establish a therapeutically effective amount of a pharmaceutical composition comprising one of the present compounds for preventing and/or treating nerve agent exposure.

Exemplary dosages in accordance with the teachings of the present invention for these compounds range from 0.0001 mg/kg to 60 mg/kg, though alternative dosages are contemplated as being within the scope of the present invention. The present oximes can, for example, be administered in amounts of 100 µmol/kg. Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

EXAMPLES

Example 1

Synthesis of Novel Oximes

A series of substituted phenoxyalkyl-pyridinium-4-aldoximes was prepared as shown below.

where: R is variable, X = Br or I, n = 3-6

Identity of the compounds was established and purity estimated by thin layer chromatography and UV absorbance by comparison to known compounds, and for some compounds by NMR and HPLC-MS.

Example 2

In Vitro AChE Reactivation

Modifications of the spectrophotometric technique of Ellman et al. (Ellman et al., 1961; Chambers et al., 1988) were used to assess reactivation efficacy and involve assay of AChE. A 1,000 g pellet of bovine brain homogenate was chosen for use in testing because the tissue was readily available, frozen pellets are stable for up to a year at −70 degrees C., and the AChE may be isolated from the reaction mixture by relatively brief centrifugation.

Assay of potential reactivators in vitro consisted of 4 steps:

(1) Incubation of AChE with organophosphate (OP). Resuspended bovine brain pellets (from a 1000 g, 10 min centrifugation) were incubated at 37 degrees C. for 10 min with $IC_{80}$ final concentration of OP (10 μl OP in ethanol/ml enzyme preparation). Control samples received ethanol only.

(2) Incubation with oxime. After initial incubation, a range of oxime concentrations were added. Inhibition standard samples received solvent only for comparison of the samples with oximes. Incubation times ranged from 5 to 30 min. at 37 degrees C.

(3) Isolation of AChE. Brain membranes were sedimented by centrifugation (1,000 g, 10 min) as in the original preparation.

(4) Assay of AChE. Resuspended pellets were assayed for AChE activity using acetylthiocholine as substrate and DTNB as chromogen (modified Ellman method). Inhibition was calculated vs. control samples and reactivation was calculated as decrease in % inhibition.

Following the above experiments with bovine brain, the present oximes were retested with a rat brain preparation using the same experimental design to verify their efficacy as reactivators in a second species. Three (3) replications of each oxime with each OP were performed.

Example 3

Determining Partition Coefficients

Lipophilicity, reflecting the potential for crossing the blood-brain barrier, was measured by determining partition coefficients. n-Octanol/water partition coefficients were determined. Oxime was dissolved in distilled water and the solution was shaken vigorously with an equal volume of the alcohol. The alcohol phase was dried over anhydrous sodium sulfate, and the oxime concentration was determined by measuring the UV absorbance and comparing to a previously established standard curve. Three (3) determinations of each oxime were performed.

Example 4

In Vivo Studies

The in vivo studies in rats were conducted in two phases: (1) determination of appropriate OP dosages, and (2) assay of reactivator efficacy. Young adult males, Sprague Dawley-derived strain, of about 150-200 g body weight, were used for these studies. This is a rat strain upon which a large data base on OP toxicology has been developed.

(1) Determination of Appropriate OP Dose.

These initial studies determined the dosage of NIMP which would give 70-80% peak inhibition of brain AChE (or the highest % inhibition possible without mortality). A high level of brain AChE inhibition is the level of poisoning that would be the most critical test of whether the oximes are effective, and would reflect the type of scenario for which a centrally-effective oxime is most needed. Since the goal of these experiments is to screen for efficacy as brain AChE reactivators, multiple LD50 levels of OP exposure were not studied because there would be excess levels of OP in circulation which would be available for an extended time to reinhibit AChE.

In addition to the overall magnitude of the inhibition, the time to maximal (or near maximal) % inhibition was also determined. The present experimental design administered the oxime after the OP had inhibited available phosphorylation sites (i.e., after the time of maximal inhibition) and was in the process of being excreted. With this design, any reduced AChE inhibition observed in the brain following oxime treatment allows a conclusion with confidence that the effect is the result of reactivation from the oxime.

Range finding studies were then performed with NIMP, administering it intraperitoneally in a DMSO/propylene glycol (1:1) vehicle that is routinely used for OP administration, using an up-and-down approach with as few animals as necessary to establish the appropriate range. Once the dosage that yielded about 70-80% brain AChE was approximated by this approach, a group of 5-6 animals was treated with that dosage as well as concurrent vehicle controls to verify that the dosage yielded a consistent level of AChE inhibition (atropine was not necessary for survival). Subsequently, a time course study with this dosage was conducted, investigating time points between 15 minutes and 4 hours following injection of the OP, to estimate the time of peak effects. The time to peak effects was determined to be 1 hour.

(2) Assay of Reactivators.

Initial tests of novel oxime toxicity. The direct toxicity of the novel oximes was tested to ensure that they are not inherently toxic themselves. Initially, the oximes were administered in equimolar dosages (100 μmol/kg) as is typically done in other oxime studies (Kassa, 1995; Kassa and Bajgar, 1998; Kassa and Cabal, 1999; Krejcova-Kunesova et al., 2005). AChE activity in the brain was measured to ensure that the oxime treatment had no effect on AChE activity; no effect of AChE activity was observed.

In vivo experiments in rats. In these experiments, the dosage of NIMP which was determined in the experiments described above to be 0.325 mg/kg was used. This dosage yielded about 80% brain acetylcholinesterase inhibition and resulted in signs of anticholinesterase poisoning, including seizures, but which was sublethal and did not require the co-administration of atropine. Oxime treatment occurred at the time when maximal brain AChE inhibition is reached as determined in the above experiments to be 1 hour. The activity of brain, erythrocyte and diaphragm AChE were measured at 30 min and 2 hours post oxime treatment. These tissues were indices of central (brain) and peripheral (diaphragm, erythrocyte) reactivation. The 30 min and 2 hr time points give an indication of whether reactivation occurs at a rate fast enough to be of therapeutic value. Oxime dose was 100 μmol/kg, the same dose used in Kassa and Cabal (1999). Oximes were dissolved in DMSO, and administered intramuscularly, to reflect the route that would be of practical use to the military. 2-PAM, the currently-accepted therapeutic oxime in the United States, was used as the standard to which the novel oximes were compared. Five to six (5-6) replications of each set of conditions were performed.

Results. The results of the foregoing experiments are shown in Tables 2 and 3 below. Table 2 shows in vitro data on reactivation by fifty-seven novel oximes of rat brain AChE inhibited by the satin surrogate PIMP and the VX surrogate NEMP. The preliminary findings with these initial oximes found that they were effective in vitro as reactivators of AChE, with some oximes approaching the efficacy of 2-PAM as a reactivator, and that they were all more lipophilic than 2-PAM with some being up to 32-fold more lipophilic than 2-PAM.

TABLE 2

Characterization of novel oximes by in vitro methods.

| Oxime | % Bovine Brain Reactivation *PIMP | % Rat Brain Reactivation *PIMP | % Rat Brain Reactivation *NEMP | Lipophilicity **P Oct/H$_2$O |
|---|---|---|---|---|
| 2-PAM | 100% | 91% | 88% | 0.006 |
| TMB-4 | 99% | 98% | 80% | <0.001 |
| Oxime 14 | 65% | 54% | 52% | 0.128 |
| Oxime 19 | 59% | 37% | 32% | 0.020 |
| Oxime 26 | 72% | 34% | 33% | 0.018 |
| Oxime 27 | 69% | 38% | 34% | 0.031 |
| Oxime 11 | 67% | 53% | 53% | 0.017 |
| Oxime 32 | 70% | 65% | 67% | 0.184 |
| Oxime 1 | 71% | 37% | 41% | 0.029 |
| Oxime 2 | 54% | 41% | 35% | 0.084 |
| Oxime 12 | 73% | 30% | 35% | 0.042 |
| Oxime 15 | 46% | 39% | 34% | 0.146 |
| Oxime 29 | 79% | 34% | 31% | 0.034 |
| Oxime 31 | 62% | 65% | 57% | 0.138 |
| Oxime 25 | 52% | 40% | 27% | 0.009 |
| Oxime 30 | 79% | 48% | 40% | 0.056 |
| Oxime 46 | 78% | 78% | 62% | 0.117 |
| Oxime 47 | 82% | 72% | 69% | 0.174 |
| Oxime 48 | 80% | 71% | 56% | 0.318 |
| Oxime 59 | 39% | 53% | 47% | 0.352 |
| Oxime 50 | 46% | 72% | 76% | 0.172 |
| Oxime 20 | 58% | 46% | 37% | 0.031 |
| Oxime 35 | 17% | 24% | 25% | 0.680 |
| Oxime 5 | 48% | 49% | 53% | 0.072 |
| Oxime 71 | 44% | 71% | 74% | 0.489 |
| Oxime 67 | 42% | 38% | 48% | 0.259 |
| Oxime 70 | 56% | 55% | 62% | 0.183 |
| Oxime 8 | 45% | 52% | 58% | 0.465 |
| Oxime 44 | 34% | 54% | 61% | 0.298 |
| Oxime 74 | 41% | 38% | 37% | 0.094 |
| Oxime 68 | 53% | 56% | 67% | 0.263 |
| Oxime 64 | 61% | 56% | 44% | 0.176 |
| Oxime 76 | 43% | 54% | 70% | 0.236 |
| Oxime 77 | 35% | 65% | 65% | 2.104 |

TABLE 2-continued

Characterization of novel oximes by in vitro methods.

| Oxime | % Bovine Brain Reactivation *PIMP | % Rat Brain Reactivation *PIMP | % Rat Brain Reactivation *NEMP | Lipophilicity **P Oct/H$_2$O |
|---|---|---|---|---|
| Oxime 10 | 40% | 35% | 45% | 0.009 |
| Oxime 16 | 50% | 51% | 62% | 0.061 |
| Oxime 17 | 50% | 57% | 67% | 0.112 |
| Oxime 18 | 45% | 41% | 45% | 0.269 |
| Oxime 39 | 42% | 49% | 56% | 0.104 |
| Oxime 53 | 37% | 31% | 42% | 0.468 |
| Oxime 56 | 27% | 34% | 35% | 0.562 |
| Oxime 86 | 36% | 33% | 41% | 0.017 |
| Oxime 65 | 60% | 53% | 48% | 0.154 |
| Oxime 37 | 34% | 47% | 55% | 0.138 |
| Oxime 58 | 32% | 43% | 46% | 0.170 |
| Oxime 60 | 26% | 29% | 36% | 0.416 |
| Oxime 99 | NT | 51% | 56% | 1.461 |
| Oxime 62 | 40% | 51% | 55% | 0.481 |
| Oxime 38 | 32% | 67% | 66% | 0.212 |
| Oxime 89 | NT | 40% | 19% | 0.359 |
| Oxime 92 | NT | 18% | 25% | 2.000 |
| Oxime 95 | NT | 36% | 33% | 0.921 |
| Oxime 113 | NT | 31% | 36% | 1.727 |
| Oxime 98 | NT | 41% | 45% | 1.076 |
| Oxime 110 | NT | 46% | 69% | 0.301 |
| Oxime 94 | NT | 38% | 53% | 0.517 |
| Oxime 63 | NT | NT | 60% | 0.666 |
| Oxime 117 | NT | NT | 46% | 0.413 |
| Oxime 116 | NT | 46% | 57% | 1.046 |

*30-min incubation with 100 μM oxime following 15-min incubation with OP
**P Octanol/water partition coefficient
**P Octanol/water partition coefficient
PIMP = phthalimidyl isopropyl methylphosphonate (sarin surrogate)
NEMP = nitrophenyl ethyl methylphosphonate (VX surrogate)
2-PAM and TMB-4 included for comparison.

Table 3 shows the results of in vivo tests in rats using the sarin surrogate NIMP. These results show that the chemistries of the present compounds can cross the blood-brain barrier and have efficacy as reactivators of brain acetylcholinesterase inhibited by sarin and potentially other nerve agents and OP insecticides. Oxime number 59 in particular displayed about 35% acetylcholinesterase reactivation in rat brains in vivo. A toxicity test was also conducted with this oxime and no toxicity was apparent at one week following oxime administration.

TABLE 3

In vivo reactivation of rat brain cholinesterase following novel oxime administration in rats treated with the sarin surrogate nitrophenyl isopropyl methylphosphonate (NIMP).

| Oxime # | 30 min reactivation | 2 hour reactivation |
|---|---|---|
| Oxime 14 | 15% | 30% |
| Oxime 27 | 0% | 0% |
| Oxime 32 | 18% | 31% |
| Oxime 31 | 7% | 30% |
| Oxime 47 | 0% | 0% |
| Oxime 48 | 0% | 0% |
| Oxime 59 | 25% | 35% |
| Oxime 50 | 4% | 10% |
| Oxime 71 | 2% | 7% |
| Oxime 67 | 8% | 13% |
| Oxime 70 | 4% | 25% |
| Oxime 8 | 3% | 10% |
| Oxime 44 | 5% | 17% |
| Oxime 74 | 4% | 14% |
| Oxime 68 | 0% | 7% |
| Oxime 64 | 2% | 2% |
| Oxime 76 | 8% | 8% |

TABLE 3-continued

In vivo reactivation of rat brain cholinesterase following novel oxime administration in rats treated with the sarin surrogate nitrophenyl isopropyl methylphosphonate (NIMP).

| Oxime # | 30 min reactivation | 2 hour reactivation |
|---|---|---|
| Oxime 77 | 0% | 5% |
| Oxime 16 | 5% | 8% |
| Oxime 17 | 3% | 6% |
| Oxime 99 | 7% | 13% |

The data in Table 4 below indicate that NIMP is of a similar potency in vivo anticholinesterase as paraoxon. The amount of brain AChE inhibition in rats obtained at 30 minutes after intraperitoneal administration of NIMP and paraoxon, the latter being a well-characterized potent anticholinesterase, were compared. The fact that NIMP leaves AChE phosphorylated by the same moiety as does sarin makes this a highly suitable surrogate to be used in the initial screening of the novel oximes.

TABLE 4

| Treatment | AChE Activity, nmoles/min/mgP | Percent Inhibition |
|---|---|---|
| Control | 92 | 0 |
| NIMP 0.25 mg/kg | 27 | 70 |
| NIMP 0.5 mg/kg | 18 | 80 |
| NIMP 1.0 mg/kg | 8 | 92 |
| Paraoxon 0.25 mg/kg | 48 | 47 |
| Paraoxon 0.5 mg/kg | 32 | 65 |
| Paraoxon 0.75 mg/kg | 3 | 96 |

Example 5

In Vivo Testing of Oxime 59

Figure 1:
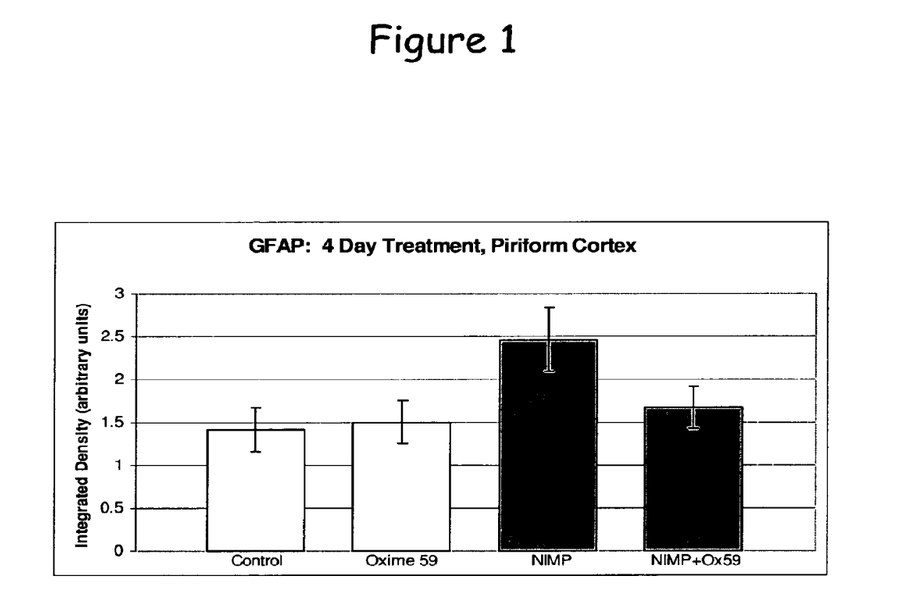
FIG. 1 is a graph showing integrated density of glial fibrillary acidic protein (GFAP) in the piriform cortex of rats 4 days post-treatment with dimethyl sulfoxide (DMSO) vehicle control, oxime 59, nitrophenyl isopropyl methylphosphonate (NIMP) (sarin surrogate), and oxime 59 administered 1 hour after dosing with NIMP (NIMP+Ox59).

Oxime 59 was further tested in vivo in rats against NIMP and NEMP. The sarin surrogate, NIMP, produced seizures in rats in the in vivo tests and yielded brain damage as indicated by the accumulation of glial fibrillary acidic protein (GFAP; a marker of inflammation indicating the initiation of damage to the brain) in the piriform cortex of the rats. Oxime 59 attenuated seizures and attenuated the accumulation of GFAP. FIG. 1 is a graph showing integrated density of GFAP in the piriform cortex of rats 4 days post-treatment with: DMSO vehicle control; oxime 59; NIMP (sarin surrogate); and oxime 59 administered 1 hour after dosing with NIMP (NIMP+Ox59). Rats treated with NIMP and oxime 59 exhibited significantly less accumulation of GFAP compared to those treated with NIMP alone.

Figure 2:
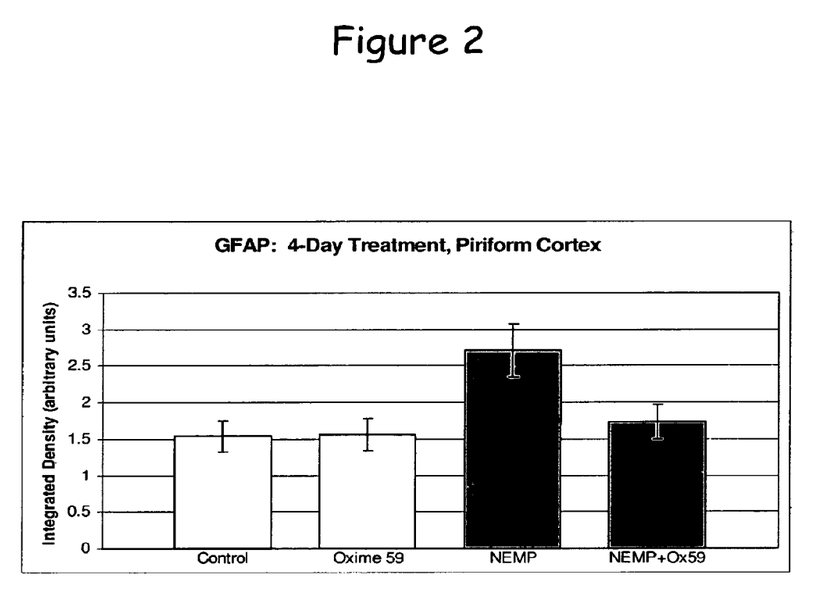
FIG. 2 is a graph showing integrated density of GFAP in the piriform cortex of rats 4 days post-treatment with DMSO vehicle control, oxime 59, nitrophenyl ethyl methylphosphonate (NEMP) (VX surrogate), and oxime 59 administered 1 hour after dosing with NEMP (NEMP+Ox59).

FIG. 2 shows the results of a similar test using NEMP. In this test the integrated density of GFAP in the piriform cortex of rats 4 days post-treatment, with oxime 59 being administered 1 hour after dosing with NEMP (the NEMP+Ox59 bar), showed much less accumulation of GFAP compared to the rats dosed only with NEMP.

Figure 3:
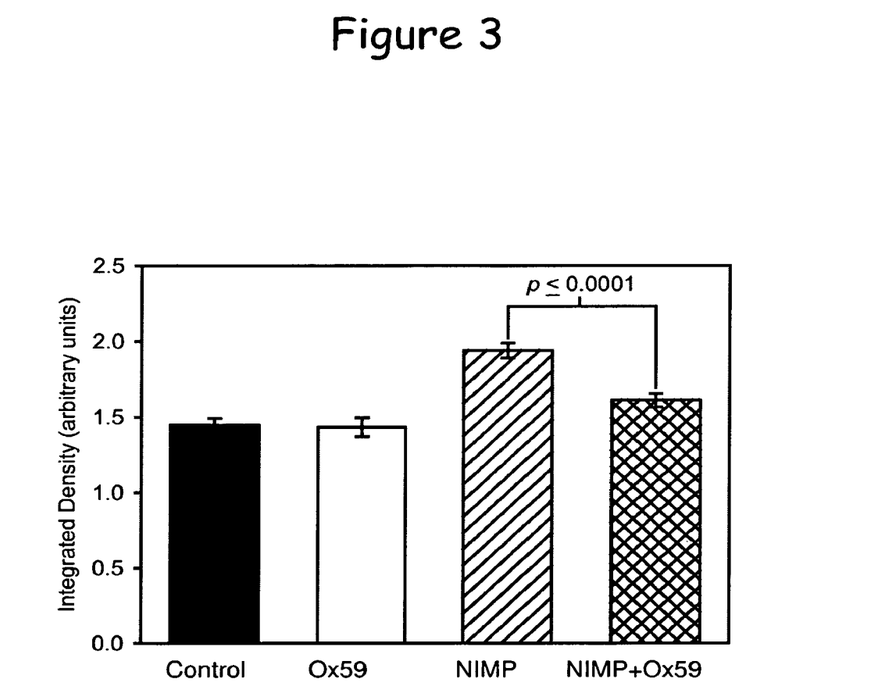
FIG. 3 is a graph showing relative concentration of GFAP in rats 2 days post-treatment with DMSO vehicle control, oxime 59, NIMP (sarin surrogate), and oxime 59 administered 1 hour after dosing with NIMP (NIMP+Ox59).

FIG. 3 is a graph of the results of a further test, showing the relative concentration of glial fibrillary acidic protein (GFAP) in rats 2 days post-treatment with: DMSO vehicle control; oxime 59; NIMP (sarin surrogate); and oxime 59 administered 1 hour after dosing with NIMP (NIMP+Ox59). Damage due to NIMP was significantly reduced by oxime 59 (P<0.001).

The above detailed description is presented to enable any person skilled in the art to make and use the invention. Descriptions of specific applications, analyses, and calculations are meant to serve only as representative examples. Various modifications to the preferred embodiments may be readily apparent to one skilled in the art, and the general principles defined herein may be applicable to other embodiments and applications while still remaining within the scope of the invention. Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A pharmaceutical composition comprising a compound having the following formula:

wherein:
(a) R is hydrogen, alkyl, alkenyl, aryl, alkoxy, aryloxy, acyl, nitro, or halo;
(b) n is 3, 4, or 5; and
(c) X is a pharmaceutically acceptable anion;
with the proviso that (1) when R is 4-$CH_3CO$—, n is not 5 and (2) when R is 4-Ph-CO—, n is neither 4 nor 5.

2. The composition of claim 1, wherein R is methyl, ethyl, phenyl, methoxy, ethoxy, trimethyl, methylchloro, diethyl, diethylchloro, ethylchloro, phenoxy, acetyl, benzoyl, bromo, chloro, iodo, dichloro, or trichloro.

3. The composition of claim 1, wherein R is one of the following substituents:
2,6-$([CH_3]_2CH)_2$—;
4-Cl—;
4-Br—;
3-CH=CHCH=CH—4;
2,3,5-$(CH_3)_3$—;
3-$CH_3$-4-Cl—;
2,5-$Cl_2$—;
4-Ph-$CH_2$—;
4-Ph-$CH_2$—O—;
2,4,6-$Cl_3$—;
3,4-$Cl_2$—;
2,6-$Cl_2$-4-$O_2$N—;
3-O—C(:O)—CH=C($CH_3$)-4; or
4-$(CH_3)_3CCH_2C(CH_3)_2$—.

4. The composition of claim 1, wherein X is halo.

5. The composition of claim 4, wherein the composition comprises a pharmaceutically acceptable excipient in combination with the compound.

6. The composition of claim 1, wherein the composition comprises a pharmaceutically acceptable excipient in combination with the compound.

7. The composition of claim 1, wherein R is 4-Cl— and n is 4.

8. The composition of claim 1, wherein R is 4-Ph-$CH_2$—O— and n is 4.

9. The composition of: claim 1, wherein R and n are selected from the group consisting of:
R is 2,6-$[CH_3]_2CH)_2$— and n is 4;
R is 4-Cl— and n is 4;

R is 4-Br— and n is 4;
R is 3-CH=CHCH=CH-4 and n is 3;
R is 3-CH=CHCH=CH-4 and n is 4;
R is 3-CH=CHCH=CH-4 and n is 5;
R is 2,3,5-$(CH_3)_3$— and n is 5;
R is 3-$CH_3$-4-Cl— and n is 4;
R is 2,5-$Cl_2$— and n is 4;
R is 4-Ph-$CH_2$— and n is 4;
R is 4-Ph-$CH_2$—O— and n is 4;
R is 2,4,6-$Cl_3$— and n is 3;
R is 2,4,6-$Cl_3$— and n is 4;
R is 3,4-$Cl_2$— and n is 3;
R is 3,4-$Cl_2$— and n is 4;
R is 2,6-$Cl_2$-4-$O_2$N— and n is 4;
R is 3-O—C(:O)—CH=C($CH_3$)-4 and n is 5; and
R is 4-$(CH_3)_3CCH_2C(CH_3)_2$— and n is 5.

10. The composition of claim 9, wherein X is halo.

11. The composition of claim 9, wherein the composition comprises a pharmaceutically acceptable excipient in combination with the compound.

12. A method of reactivating phosphorylated brain acetylcholinesterase that has been inhibited by at least one organophosphorous compound, the method comprising administering to a subject in need thereof a therapeutically effective amount of the pharmaceutical composition comprising a compound having the following formula:

wherein:
(a) R is hydrogen, alkyl, alkenyl, aryl, alkoxy, aryloxy, acyl, nitro, or halo;
(b) n is 3, 4, or 5; and
(c) X is a pharmaceutically acceptable anion;
with the proviso that (1) when R is 4-$CH_3$CO—, n is not 5 and 2 when R is 4-Ph-CO—, n is neither 4 nor 5.

13. The method of claim 12, wherein the composition is administered by an administrative route selected from the group consisting of intravenous, oral, topical, intraperitoneal, transdermal, nasal, rectal, vaginal, intramuscular, and subcutaneous.

14. The method of claim 12, wherein the therapeutically effective amount of the compound is administered to the subject following exposure of the subject to the organophosphorous compound.

15. A method of treating the effects of exposure to an organophosphate compound, comprising administering to a subject in need thereof a therapeutically effective amount of a pharmaceutical composition comprising a compound having the following formula:

wherein:
(a) R is hydrogen, alkyl, alkenyl, aryl, alkoxy, aryloxy, acyl, nitro, or halo;
(b) n is 3, 4, or 5; and
(c) X is a pharmaceutically acceptable anion;
with the proviso that (1) when R is 4-$CH_3$CO—, n is not 5 and (2) when R is 4-Ph-CO—, n is neither 4 nor 5.

16. The method of claim 15, wherein the composition is administered by an administrative route selected from the group consisting of intravenous, oral, topical, intraperitoneal, transdermal, nasal, rectal, vaginal, intramuscular, and subcutaneous.

17. The method of claim 15, wherein the therapeutically effective amount of the compound is administered to the subject following exposure of the subject to the organophosphate compound.

18. The method of claim 15, wherein the therapeutically effective amount of the compound is administered to the subject prior to exposure of the subject to the organophosphate compound.

19. The method of claim 15, wherein the organophosphate compound is an insecticide.

20. The method of claim 15, wherein the organophosphate compound is sarin, soman, tabun, or VX.

* * * * *